United States Patent
Schwartz et al.

(10) Patent No.: US 9,883,791 B2
(45) Date of Patent: Feb. 6, 2018

(54) DISPOSABLE SHEATH FOR AN ENDOTRACHEAL INTUBATION DEVICE

(71) Applicant: Centurion Medical Products Corporation, Williamston, MI (US)

(72) Inventors: John Schwartz, Williamston, MI (US); Richard Schwartz, Evans, GA (US); Harsha Setty, Fortson, GA (US); Christopher Montgomery, High Springs, FL (US)

(73) Assignee: Blink Device, LLC, Okemos, MI (US)

( * ) Notice: Subject to any disclaimer, the term of this patent is extended or adjusted under 35 U.S.C. 154(b) by 478 days.

(21) Appl. No.: 14/501,294

(22) Filed: Sep. 30, 2014

(65) Prior Publication Data
US 2015/0099933 A1    Apr. 9, 2015

Related U.S. Application Data

(60) Provisional application No. 61/888,331, filed on Oct. 8, 2013.

(51) Int. Cl.
*A61B 1/267* (2006.01)
*A61M 16/04* (2006.01)

(52) U.S. Cl.
CPC ......... *A61B 1/267* (2013.01); *A61M 16/0488* (2013.01); *A61M 2205/0216* (2013.01)

(58) Field of Classification Search
CPC ....... A61B 1/005–1/0058; A61B 1/008; A61B 1/267; A61B 1/0673; A61B 1/0676
USPC .................................................. 600/185–199
See application file for complete search history.

(56) References Cited

U.S. PATENT DOCUMENTS

| 2,975,785 | A |   | 3/1961 | Sheldon |
|---|---|---|---|---|
| 4,529,400 | A |   | 7/1985 | Scholten |
| 4,567,882 | A | * | 2/1986 | Heller .................. A61M 25/01 |
|   |   |   |   | 128/200.26 |

(Continued)

FOREIGN PATENT DOCUMENTS

| EP | 2403395 A1 | 1/2012 |
|---|---|---|
| EP | 2481345 A1 | 8/2012 |

(Continued)

OTHER PUBLICATIONS

PCT International Search Report & Written Opinion dated Apr. 12, 2016 for PCT/US2014/058249.

(Continued)

*Primary Examiner* — Eric S Gibson
(74) *Attorney, Agent, or Firm* — Kristin L. Murphy; Brooks Kushman P.C.

(57) ABSTRACT

A sheath for an endotracheal intubation device includes an elongate flexible portion defining a closed conduit and an adjacent open channel defined by opposing lips for releasably retaining an endotracheal tube, and a rigid portion extending from a distal end of the flexible portion, the flexible portion including a gap in one of the lips adjacent the rigid portion to expose an edge of the rigid portion, the gap allowing the endotracheal tube to be pinched between the edge of the rigid portion and a lip of the flexible portion to enhance retention of the tube when an articulated arm disposed in the closed conduit is curved, and facilitate release of the tube when the arm is not curved.

20 Claims, 4 Drawing Sheets

(56) References Cited

U.S. PATENT DOCUMENTS

| | | | |
|---|---|---|---|
| 6,539,942 B2 * | 4/2003 | Schwartz | A61M 16/0488 128/207.14 |
| 7,458,375 B2 | 12/2008 | Schwartz et al. | |
| 7,658,708 B2 | 2/2010 | Schwartz et al. | |
| 8,042,545 B2 | 10/2011 | Schwartz et al. | |
| 8,231,524 B2 | 7/2012 | Schwartz et al. | |
| 8,336,541 B2 | 12/2012 | Schwartz et al. | |
| 8,764,638 B2 | 7/2014 | Schwartz et al. | |
| 9,414,743 B2 * | 8/2016 | McGrath | A61M 16/0488 |
| 2002/0022769 A1 | 2/2002 | Smith | |
| 2007/0106121 A1 | 5/2007 | Yokota | |
| 2008/0017195 A1 | 1/2008 | Yoshida | |
| 2008/0045802 A1 * | 2/2008 | Brandstaetter | A61B 1/0607 600/199 |
| 2008/0200761 A1 | 8/2008 | Schwartz et al. | |
| 2008/0308098 A1 | 12/2008 | Schwartz et al. | |
| 2009/0143645 A1 | 6/2009 | Matthes | |
| 2010/0137687 A1 | 6/2010 | Schwartz et al. | |
| 2010/0256451 A1 * | 10/2010 | McGrath | A61B 1/267 600/185 |
| 2011/0196204 A1 * | 8/2011 | Setty | A61B 1/00052 600/120 |
| 2011/0245609 A1 * | 10/2011 | Laser | A61B 1/00052 600/109 |
| 2011/0306839 A1 * | 12/2011 | Young | A61B 1/00052 600/188 |
| 2011/0313243 A1 * | 12/2011 | Zubiate | A61B 1/008 600/104 |
| 2012/0059223 A1 * | 3/2012 | McGrath | A61B 1/267 600/185 |
| 2012/0078050 A1 | 3/2012 | Schwartz et al. | |
| 2012/0095294 A1 * | 4/2012 | Mcgrath | A61B 1/267 600/188 |
| 2012/0259176 A1 * | 10/2012 | Grey | A61B 1/00105 600/188 |
| 2014/0275766 A1 | 9/2014 | Schwartz et al. | |
| 2015/0099933 A1 * | 4/2015 | Schwartz | A61M 16/0488 600/186 |

FOREIGN PATENT DOCUMENTS

| | | |
|---|---|---|
| WO | 20070138569 A1 | 12/2007 |
| WO | 2008127994 A1 | 10/2008 |
| WO | 2010100495 A1 | 9/2010 |

OTHER PUBLICATIONS

Supplementary European Search Report dated Apr. 11, 2017 for EP14852083.

* cited by examiner

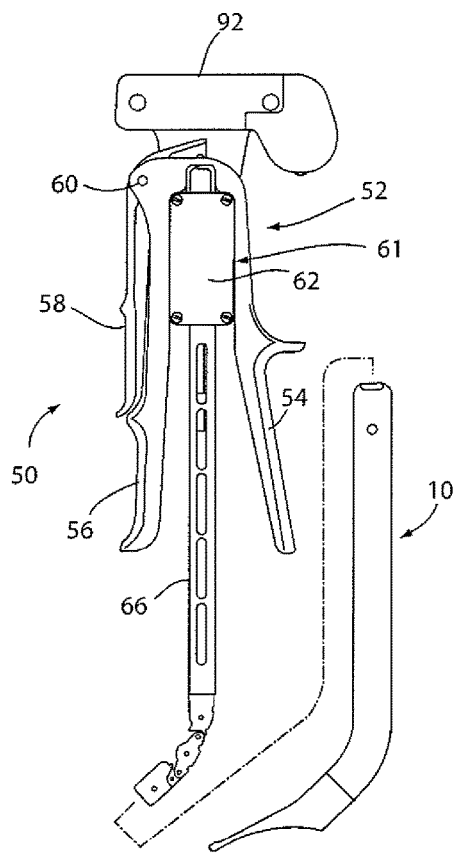
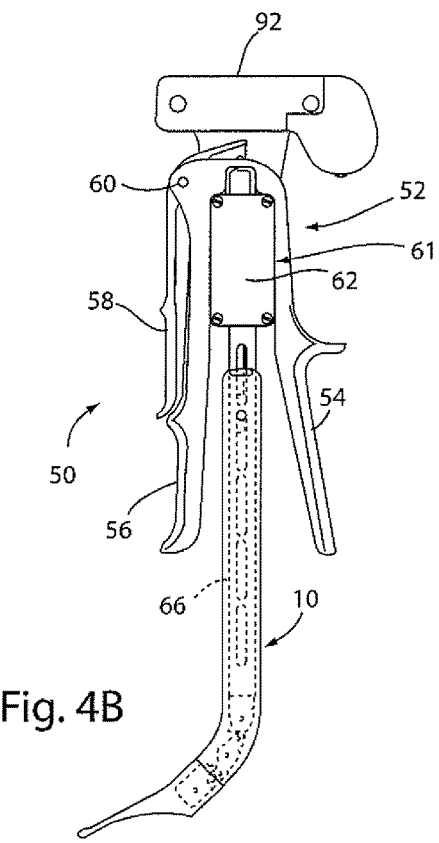
Fig. 4A
Fig. 4B
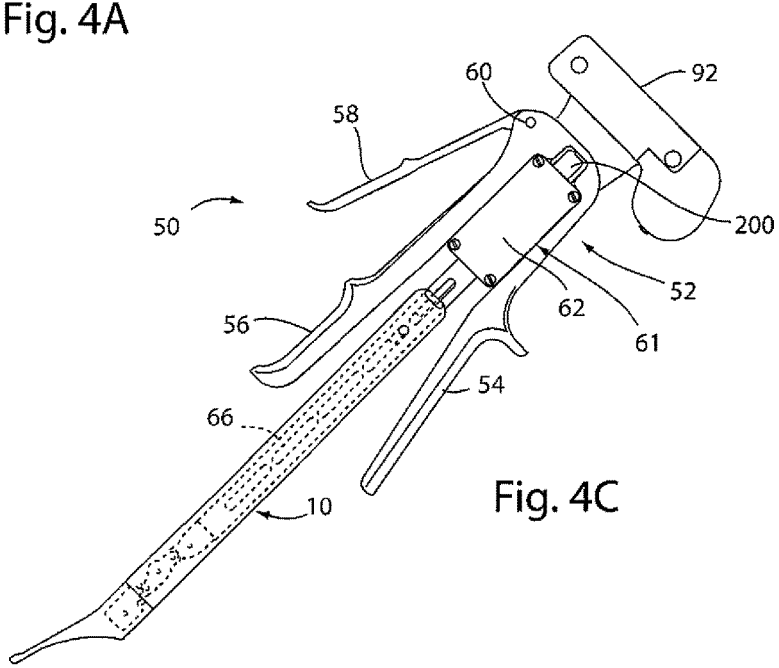
Fig. 4C

DISPOSABLE SHEATH FOR AN ENDOTRACHEAL INTUBATION DEVICE

CROSS-REFERENCE TO RELATED APPLICATIONS

This application claims the benefit of U.S. Provisional Application No. 61/888,331, filed Oct. 8, 2013, which is incorporated herein by reference.

FIELD OF THE DISCLOSURE

This disclosure relates to endotracheal intubation devices, and more particularly to an endotracheal intubation device that can be easily and quickly prepared for reuse.

BACKGROUND OF THE DISCLOSURE

Endotracheal intubation devices having a manipulated (e.g., curvable) distal end that facilitates guiding of an endotracheal tube into a trachea of a patient are known. It is also known to employ a flexible sheath over the distal portion of the device, which can be discarded at the end of an intubation process and replaced with a new sheath before the device is used again. This arrangement reduces or eliminates the need for sterilization and/or disinfection of the instrument between procedures.

SUMMARY OF THE DISCLOSURE

A sheath for an endotracheal intubation device in accordance with this disclosure includes an elongate flexible portion defining a longitudinally extending conduit for receiving an elongate articulated arm having a distal curvable end opposite a proximal end coupled to a handle, and an open channel defined adjacent the conduit by a pair of lips that extend from a wall of the conduit to form a C-shaped profile for releasably retaining an intubation tube. The sheath also includes a rigid portion extending from a distal end of the flexible portion.

In certain embodiments, a plurality of resilient clips are disposed in spaced apart relationship along the length of the open channel to enhance retention of an intubation tube in the channel.

In certain embodiments, a gap is defined along a section of one of the lips, such as at the distal end of the flexible portion to pinch a tube in the channel and enhance retention while the distal end of the articulated arm is curved.

These and other features, advantages and objects of the various embodiments will be better understood with reference to the following specification and claims.

BRIEF DESCRIPTION OF THE DRAWINGS

FIG. 4A is a side view of an endotracheal intubation device which is usable with the sheath.

FIG. 4B is a side view of the endotracheal intubation device of FIG. 4A with the sheath of FIG. 1 disposed over the articulated arm of the device, and the lever in a compressed position causing the articulated arm to bend to a relatively curved configuration.

FIG. 4C is a side view of the endotracheal intubation device of FIG. 4B with the lever in a released position causing the articulated arm to relax to a relatively straight (non-curved) configuration.

DETAILED DESCRIPTION OF THE DISCLOSED EMBODIMENTS

Figure 1:
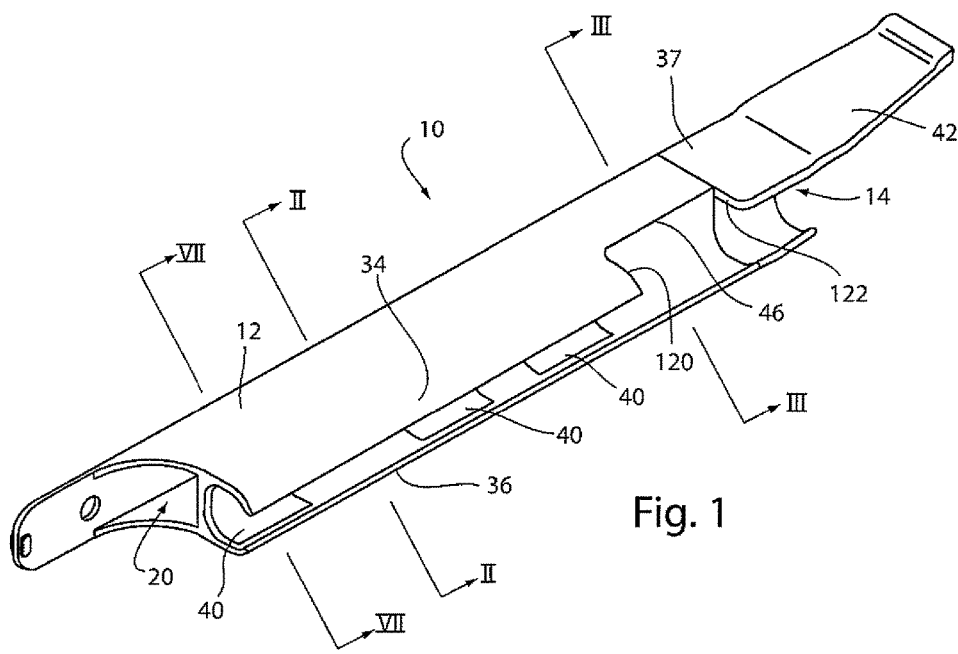
FIG. 1 is a perspective view of a sheath for an endotracheal intubation device in accordance with this disclosure.

The single-use, disposable sheath 10 for an articulable endotracheal intubation device is illustrated in FIG. 1. Sheath 10 includes a relatively flexible portion 12 constituting the majority of the length of the sheath and a relatively rigid portion 14 at the distal end of the sheath. Together, and individually, the flexible and rigid portions define a longitudinally extending conduit 20 that is sized and shaped to receive a jointed or articulated arm of an intubation device having a distal curvable end that is opposite an end configured to be attached to a handle.

Although the sheath disclosed herein are described as "single-use, disposable sheaths," it is understood that this language is more descriptive of the practical and intended use of the sheaths than the structure of the sheaths. In particular, the term "single-use" is intended to mean that the sheaths are made of inexpensive materials that can be easily and economically molded into a finished component that can be economically discarded after a single intubation procedure.

The relatively flexible portion 12 of the sheath 10 is softer and more flexible than the relatively rigid portion 14 of the sheath. The flexible portion 12 can be made of a flexible rubber, such as a silicone rubber, and can have a Shore A hardness below 70, below 60, or below 50. A suitable Shore A hardness for the flexible portion 12 of sheath 10 can be from about 10 to about 70, from about 20 to 60, or from about 30 to about 50.

The relatively rigid portion 14 of the sheath 10 is harder and less flexible than the relatively flexible portion 12 of the sheath. The relatively rigid portion 14 can be made of a relatively rigid thermoplastic material, such as a polycarbonate, polystyrene, nylon, or an acrylic polymer (e.g., polymethylmethacrylate), and can have a Shore D hardness of at least 60, at least 70, or at least 80. A hardness for the relatively rigid portion 12 of sheath 10 can be from about 60 Shore D to about 150 Rockwell R, about 70 Shore D to about 150 Rockwell R, or about 80 Shore D to about 150 Rockwell R.

Figure 2:
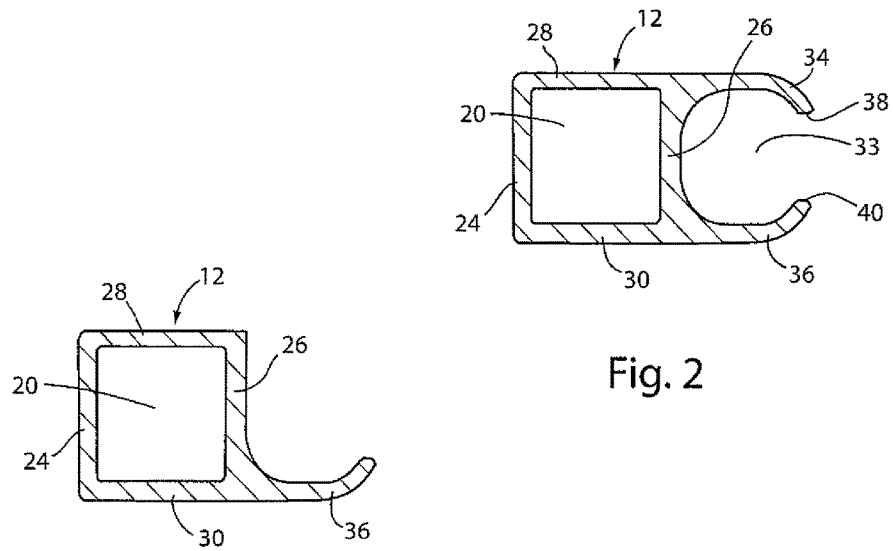
FIG. 2 is a cross-sectional view of the sheath as viewed along lines II-II of FIG. 1.

Longitudinally extending conduit 20 has a square cross-sectional shape or profile as shown in FIG. 2 of the illustrated embodiment. However, other cross-sectional shapes can be used. Conduit 20 is generally defined by a first wall 24, an opposite second wall 26, and opposing walls 28 and 30 that extend between walls 24 and 26 to define a closed structure that prevents body fluids from entering when the sheath is disposed over the articulated arm of an intubation device during an intubation procedure. The distal end of conduit 20, which is located in the trachea of a patient during an intubation procedure can include a clear optical window 32 that sealingly closes the distal end of the tube, preventing body fluids from entering conduit 20, while allowing an image of the position of the device in the trachea of a patient to be viewed during the intubation procedure, such as via a camera or imaging device located at the distal end of the articulated arm of the intubation device adjacent the window 32.

An open retaining channel 33 is defined adjacent conduit 20 by a pair of retaining lips 34, 36 that extend perpendicularly away from opposite ends of wall 26 and curve toward each other to form a C-shaped profile for retaining an intubation tube during an intubation procedure. The channel opening 33 is sized to accommodate an intubation tube having a predetermined outer diameter, with the ends 38, 40 of retaining lips 34, 36 being spaced apart by a distance (or gap) that is less than the outer diameter of the intubation tube when the lips 34, 36 are in a relaxed state (i.e., a state in which the lips 34, 36 are not flexed or distorted, but instead are in the natural conformation or configuration when there are not any applied forces).

Figure 7:
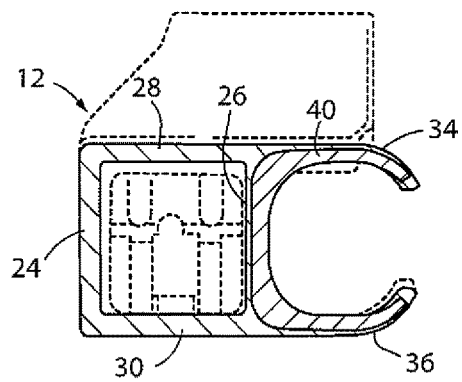
FIG. 7 is a cross-sectional view of the sheath as viewed along lines VII-VII of FIG. 1.
Figure 8:
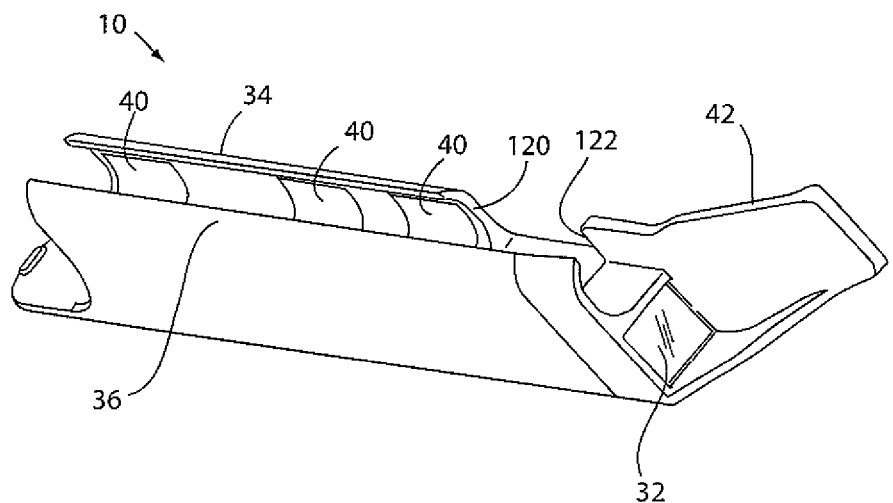
FIG. 8 is a perspective view of the distal end of the sheath showing a transparent window for a camera.

In order to maintain or enhance resilience of the retention channel during preparation for and performance of an intubation procedure, a plurality of resilient C-shaped clips 40 may be employed along the length of the retention channel. The C-shaped clips can be spaced apart to provide sections between the clips 40 into which an intubation tube can be more easily inserted and from which an intubation tube can be easily released once the tube has been satisfactorily positioned in the trachea. The clips 40 can be fully or partially embedded (see FIG. 7) in the flexible rubber material from which the portion 12 of sheath 10 is formed. Alternatively, clips 40 can be adhesively bonded to lips 34, 36 and/or wall 26, or mechanically attached to lips 34, 36, such as with tabs projecting from the clips and engaging slots through lips 34, 36. Clips 40 can be made of a deformable material that can be resilient or non-resilient. Clips 40 can exhibit less flexibility than lips 34, 36. Examples of suitable materials for clips 40 include metals (e.g., steel, stainless steel, aluminum, nickel, nickel alloys, etc.) or thermoplastic elastomers.

The relatively rigid portion 14 of sheath 10 has a first section 37 immediately adjacent a distal end of flexible portion 12 of the sheath, which has a cross-sectional shape that is substantially the same as illustrated in FIG. 2. Projecting integrally in a generally distal direction from an upper wall 12A of rigid portion 14 is a tongue elevator 42 that can be used during endotracheal intubation to lift the epiglottis of the patient as the endotracheal tube is being inserted into the trachea of the patient.

Figure 3:
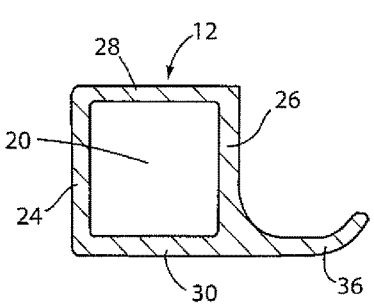
FIG. 3 is a cross-sectional view of the sheath as viewed along lines III-III of FIG. 1.

Defined at a distal end of the flexible portion 12 of sheath 10 is a cut-out section or gap 46 in lip 34. A cross-sectional profile of the distal section of flexible portion 12 is shown in FIG. 3. In this cut-out section, lip 34 is non-existent. The gap 46 generally extends over only a small fraction of the total length of the flexible portion 12 (e.g., less than 25%, less than 20%, less than 15% or less than 10%).

Shown in FIGS. 4A and 4B are side views of an intubation device 50 having a handle portion 52 including grips 54 and 56, and a lever 58 pivotably connected to handle portion 52 at pivot pin 60. In the illustrated embodiment, a detachable module 61 includes an actuator housing 62 containing an actuator assembly operatively connecting lever 58 with a spring loaded member 64 (FIG. 5) reciprocatably movable relative to the longitudinal direction of jointed arm 66.

Figure 5:
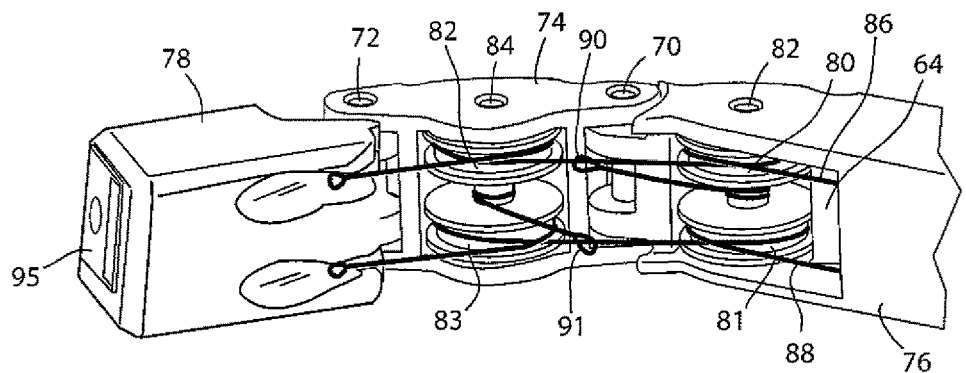
FIG. 5 is a perspective view showing detail of the articulated members of the articulated arm of the endotracheal intubation device.

As shown in FIG. 5, the jointed arm 66 includes two joints or articulations 70, 72, with a single linkage 74 hinged at one end to the main portion 76 of arm 66 and hinged at the other end to terminal member 78, which is sized and shaped to conform with and substantially fill the internal volume defined by the first section 37 of rigid portion 14, such that the distal end of flexible portion 12 of sheath 10 bends in conformance with rotational movement of linkage 74 and terminal member 78 around hinges 70 and 72, respectively, when spring loaded member 64 is actuated. Additional linkages, similar to linkage 74 may be used if desired to provide more articulations and greater ability to curve arm 66.

As can be seen in FIG. 5, the distal end of main portion 76 of arm 66 includes two pulleys 80, 81 arranged side-by-side and each rotatable around an axle 82. Linkage 74 also includes two pulleys 82, 83 arranged side-by-side and each rotatable around an axle 84. A first control wire 86 is fixed to member 64, wrapped around pulley 80, then wrapped around pulley 82, and joined to terminal member 78. A second control wire 88 is fixed to member 64, wrapped around pulley 81, then wrapped around pulley 83, and joined to terminal member 78. Guides 90 and 91 can be provided to control movement and position of wires 86 and 88 during actuation of arm 66 and bending of sheath 10 when sheath 10 is positioned over arm 66. The use of pulleys 80, 81, 82 and 83 reduces friction between the control wires and the linkage or linkages during bending of the distal end of arm 66 as compared to an arrangement in which the control wire or wires merely pass through guide openings in the linkage(s). The pulleys also provide a mechanical advantage and smoother operation without sacrificing sensitivity (i.e., the ability to accurately control bending of the distal end of arm 66 by manipulation of lever 58). A single set of pulleys (one on linkage 74 and another on terminal member 78) can be used with a single control wire if desired. However, the use of two control wires and two sets of pulleys provides a more balanced and smoother application of force to the articulated members of arm 66.

Figure 6:
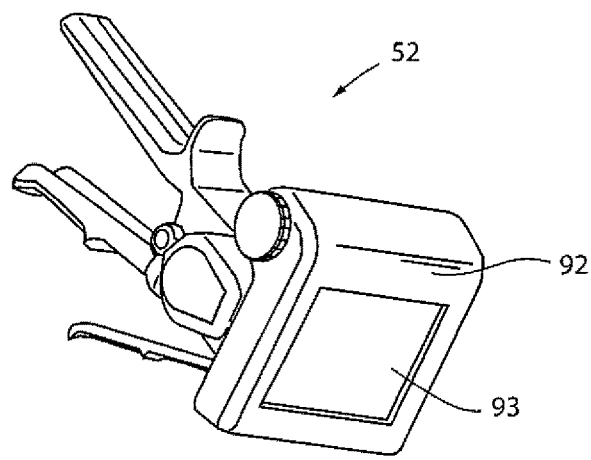
FIG. 6 is a perspective view of the endotracheal intubation device shown in FIG. 4A, illustrating the video display of the device.

As shown in FIG. 6, device 52 can include a video display device 92 having a video display screen 93 which can be connected to a camera 95 positioned on the distal end of terminal member 78 to allow a medical professional to see inside the throat and trachea of a patient during an endotracheal intubation procedure.

As indicated in FIG. 4C, lever 58 can be directly attachable to a reciprocating member 200 to which control wires 86 and 88 are attached so that when lever 58 is pressed toward grip 56, reciprocating member 200 is pulled proximally along with attached wires 86 and 88 causing the articulated members 74 and 78 to curve the distal end of arm 66 as shown in FIG. 4B.

Figure 9:
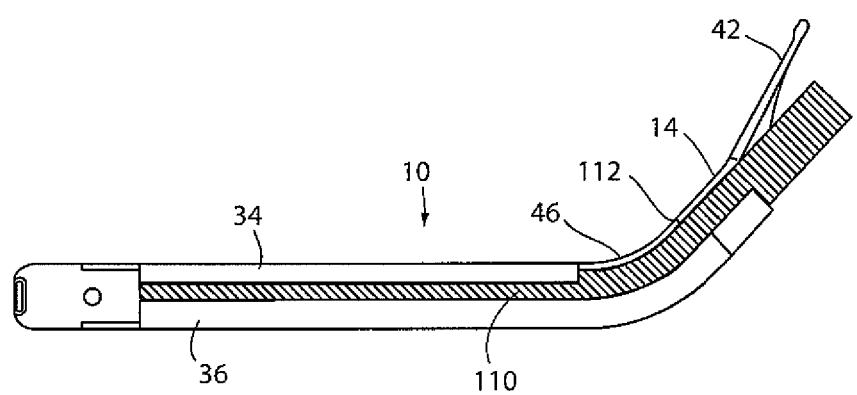
FIG. 9 is a perspective view of an endotracheal intubation device having an intubation tube pinched between an edge of the rigid section of the sheath and lip of the open channel when the articulated arm of the device is curved.

During an intubation procedure, a sheath 10 is positioned over arm 66 as shown in FIG. 4B. Thereafter, an endotracheal tube 110 is positioned in open channel 33 as shown in FIG. 9. The distal end of the device is inserted into the mouth of a patient, with the curvable distal end of the device in the straighter (less curved), relaxed position. Lever 58 can be operated during insertion as needed to curve the distal end of arm 66 and flexible sheath 10 to allow the device to be safely advanced through the throat of the patient to the trachea. As the distal end of the device is curved, a surface of tube 110 engages an edge 112 of relatively rigid portion 14 of sheath 10, which is exposed by gap 46. An opposing surface of tube 110 also engages an interior surface of lip 36.

Thus, as pressure is applied to lever 58 causing the distal end of arm 66 and sheath 10 to bend, the clearance between edge 112 and lip 36 is reduced causing tube 110 to be pinched and more tightly retained in the channel 33. When the lever 58 is released, the tension on control wires 86 and 88 is released causing the distal end of arm 66 to return to its normal (relaxed) orientation in which the distal end of arm 66 is straighter (less curved), thereby releasing the pinching or compressive force applied to tube 110 between edge 112 and lip 36, and allowing the device (i.e., handle portion 52, stylet 61 and sheath 10) to be withdrawn from the throat of the patient, while the tube 110 remains in position to ventilate the patient.

Thus, gap 46 allows strong tube retention when arm 66 is flexed or articulated causing tube 110 to be pinched and fixed at the edges 120, 122 of gap 46, and facilitates removal of the tube from the device when arm 66 is straight or relaxed.

The above description is considered that of the preferred embodiment(s) only. Modifications of these embodiments will occur to those skilled in the art and to those who make or use the illustrated embodiments. Therefore, it is understood that the embodiment(s) described above are merely exemplary and not intended to limit the scope of this disclosure, which is defined by the following claims as interpreted according to the principles of patent law, including the doctrine of equivalents.

The invention claimed is:

1. A sheath for an endotracheal intubation device, comprising:
    an elongate flexible portion defining a longitudinally extending conduit that is configured to receive an elongate articulated arm having a distal curvable end opposite a proximal end coupled to a handle, the flexible portion including an open channel defined adjacent the longitudinally extending conduit by a pair of lips that project from the flexible portion to define a longitudinally extending open channel having a C-shaped cross-section;
    a rigid portion adjacent a distal end of the flexible portion;
    at least one C-shaped clip connected to the pair of lips; and
    a gap defined along a section of one of the lips.

2. The sheath of claim 1, in which the flexible portion is comprised of a material having a Shore A hardness below 70.

3. The sheath of claim 2, in which the rigid portion has a Shore D hardness of at least 60.

4. The sheath of claim 1, in which the flexible portion is comprised of a rubber having a Shore A hardness below 70.

5. The sheath of claim 4, in which the rigid portion is comprised of a thermoplastic material having a Shore D hardness of at least 60.

6. The sheath of claim 1, in which the flexible portion is comprised of a silicone rubber having a Shore A hardness below 70, and the rigid portion is comprised of a thermoplastic material having a Shore D hardness of at least 60.

7. The sheath of claim 1, in which the thermoplastic material is selected from the group consisting of polycarbonates, acrylic polymers, polystyrene and nylon.

8. The sheath of claim 1, in which the conduit has a square cross-section.

9. The sheath of claim 1, in which the distal end of the conduit is sealingly closed with an optically clear window.

10. The sheath of claim 1, in which at least one clip comprises a plurality of resilient clips that are disposed in spaced apart relationship along the length of the open channel.

11. The sheath of claim 10, in which the clips have a C-shape that conforms with the shape of the open channel.

12. The sheath of claim 10, in which the clips are fully or partially embedded in the lips.

13. The sheath of claim 10, in which the clips are comprised of a material selected from the group consisting of steel, stainless steel, nickel, and nickel alloys.

14. The sheath of claim 10, in which the clips are comprised of a thermoplastic elastomer.

15. The sheath of claim 1, in which the gap is at a distal end of the flexible portion and exposes an edge of the rigid portion.

16. The sheath of claim 15 in which the gap is defined between an edge of the flexible portion and an edge of the rigid portion, and is configured to retain an endotracheal tube when the sheath is bent and to release the endotracheal tube when the sheath is straight.

17. The sheath of claim 1, disposed over a jointed arm coupled to a handle portion having a pivotable lever for curving the jointed arm.

18. The sheath of claim 1, in which the jointed arm includes at least two joints, and includes at least one linkage member hinged to a main unarticulated portion of the jointed arm, and a terminal member hinged to a linkage member.

19. The sheath of claim 18, in which a first control wire operatively coupled to the lever is wrapped around a first pulley rotatably mounted on the at least one linkage member, around a second pulley rotatably mounted on the terminal member, and coupled to the terminal member.

20. The sheath of claim 19, further comprising a second control wire operatively coupled to the lever, the second wire wrapped around a third pulley rotatably mounted on the at least one linkage member, around a fourth pulley rotatably mounted on the terminal member, and coupled to the terminal member.

* * * * *